US009486533B2

(12) United States Patent
Gmeiner

(10) Patent No.: US 9,486,533 B2
(45) Date of Patent: Nov. 8, 2016

(54) PHARMACEUTICAL COMPOSITIONS FOR HIGH-CAPACITY TARGETED DELIVERY

(71) Applicant: Wake Forest University Health Sciences, Winston-Salem, NC (US)

(72) Inventor: William H. Gmeiner, Yadkinville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/498,444

(22) Filed: Sep. 26, 2014

(65) Prior Publication Data
US 2015/0094359 A1 Apr. 2, 2015

Related U.S. Application Data

(60) Provisional application No. 61/883,270, filed on Sep. 27, 2013.

(51) Int. Cl.
*C07H 21/04* (2006.01)
*A61K 47/48* (2006.01)
*A61K 31/704* (2006.01)
*A61K 31/00* (2006.01)

(52) U.S. Cl.
CPC ......... *A61K 47/48092* (2013.01); *A61K 31/00* (2013.01); *A61K 31/704* (2013.01)

(58) Field of Classification Search
CPC ............... A61K 47/48092; A61K 31/704; C12N 2310/16
See application file for complete search history.

(56) References Cited

U.S. PATENT DOCUMENTS

| | | |
|---|---|---|
| 5,457,187 A | 10/1995 | Gmeiner et al. |
| 5,614,505 A | 3/1997 | Gmeiner et al. |
| 5,660,985 A | 8/1997 | Pieken et al. |
| 5,663,321 A | 9/1997 | Gmeiner et al. |
| 5,741,900 A | 4/1998 | Gmeiner et al. |
| 6,342,485 B1 | 1/2002 | Gmeiner |
| 6,613,526 B2 | 9/2003 | Heilig et al. |
| 6,699,843 B2 | 3/2004 | Pietras et al. |
| 8,940,885 B2 | 1/2015 | Gmeiner |
| 9,012,422 B2 | 4/2015 | Gmeiner et al. |
| 2004/0249130 A1 | 12/2004 | Stanton et al. |
| 2005/0245471 A1 | 11/2005 | Balloul et al. |
| 2005/0256071 A1 | 11/2005 | Davis |
| 2005/0282190 A1 | 12/2005 | Shi et al. |
| 2005/0287128 A1 | 12/2005 | Guerciolini et al. |
| 2006/0088864 A1 | 4/2006 | Smolke et al. |
| 2006/0246123 A1 | 11/2006 | Gilboa et al. |
| 2007/0009476 A1 | 1/2007 | Wilson et al. |
| 2008/0026947 A1 | 1/2008 | Gmeiner |
| 2010/0261781 A1 | 10/2010 | Gmeiner |
| 2011/0213135 A1* | 9/2011 | Gmeiner .................. C40B 20/04 536/23.1 |
| 2013/0209514 A1* | 8/2013 | Gilboa ................ A61K 39/0011 424/277.1 |
| 2014/0255471 A1 | 9/2014 | Gmeiner et al. |

FOREIGN PATENT DOCUMENTS

WO WO 2009/046104 A1 4/2009

OTHER PUBLICATIONS

Zeman et al. (PNAS 95: 11561-11565, 1998).*
Fencik J. Med. Chem. 1997, 40, 2452-2461.*
Sajjad M et al. Investigation of 3'-debenzoyl-3'-(3-([124I]-iodobenzoyl))paclitaxel analog as a radio-tracer to study multidrug resistance in vivo. Applied Radiation and Isotopes. 2012; 70: 1624-1631.
Boyacioglu O et al. Dimeric DNA aptamer complexes for high-capacity-targeted drug delivery using pH-sensitive covalent linkages. Molecular Therapy—Nucleic Acids. 2013; 2; e107, 8pp.
Wang AH et al. Formaldehyde cross-links daunorubicin and DNA efficiently: HPLC and X-ray diffraction studies. Biochemistry. Apr. 23, 1991; 30(16): 3812-3815. Abstract.
Corrias et al., "Interaction of human plasma membrane proteins and oligodeoxynucleotides", *Biochemical Pharmacology*, 1998, 55: 1221-1227.
Farokhzad et al., "Nanoparticle-aptamer bioconjugates: a new approach for targeting prostate cancer cells", *Cancer Research*, 2004, 64: 7668-7672.
Fracasso et al., "Anti-tumor effects of toxins targeted to the prostate specific membrane antigen", *The Prostate*, 2002, 53: 9-23.
Gmeiner et al., "Enhanced DNA-Directed Effects of FdUMP[10] Compared to 5FU", *Nucleosides, Nucleotides & Nucleic Acids*, 2004, 23(1-2): 401-410.
Gmeiner, William, "Novel Chemical Strategies for Thymidylate Synthase Inhibition", *Current Medicinal Chemistry*, 2005, 12: 191-202.
Liu et al., "Constitutive and Antibody-Induced Internalization of Prostate-specific Membrane Antigen", *Cancer Research*, 1981, 58: 4055-4060.
Liu et al., "Targeted drug delivery to chemoresistant cells: folic acid derivatization of fdUMP[10] enhances Cytotoxicity toward 5-FU-resistant human colorectal tumor cells", *The Journal of Organic Chemistry*, 2001, 66(17): 5655-5663.

(Continued)

*Primary Examiner* — Brian Whiteman

(74) *Attorney, Agent, or Firm* — Myers Bigel & Sibley, P.A.

(57) ABSTRACT

Provided herein are aptamers and pharmaceutical compositions comprising the same. In some embodiments, the aptamer selectively binds a protein of interest such as an extracellular receptor protein of interest (e.g., a cancer cell extracellular receptor protein, which may be differentially expressed in some embodiments). In some embodiments, the aptamer is directly linked by covalent bonding (e.g., via a geminal diamine linkage) to from 2 to 10 toxin compounds. Also provided herein is a method of selecting an aptamer that specifically binds to a protein expressed by a cell of interest, wherein in some embodiments the aptamer comprises at least one binding site for one or more active compounds. In some embodiments, primer regions flanking the variable region of the aptamers in the pool contains from 1 to 10 mismatches with respect to said forward or reverse primer.

11 Claims, 2 Drawing Sheets

(56) References Cited

OTHER PUBLICATIONS

Liu et al., "Efficacy and safety of FdUMP[10] in treatment of HT-29 human colon cancer xenografts", *Journal of Oncology*, 2002, 21: 303-308.

Loke et al., "Characterization of oligonucleotide transport into living cells", *Proceedings of the National Academy of Sciences*, 1989, 86: 3474-3478.

Longley et al., "5-Fluorouracil: Mechanisms of Action and Clinical Strategies", *Nature Publishing Group*, 2003, 3: 330-338.

Lupold et al., "Identification and Characterization of Nuclease-stabilized RNA Molecules that Bind Human Prostate Cancer Cells via the Prostate-specific Membrane Antigen", *Cancer Research*, 2002, 62: 4029-4033.

McNamara et al., "Multivalent 4-1BB binding aptamers costimulate CD8+ T cells and inhibit tumor growth in mice", *The Journal of Clinical Investigation*, 2008, 118(1): 376-386.

Morris et al., "High affinity ligands from in vitro selection: complex targets", *Proceedings of the National Academy of Sciences*, 1998, 95: 2902-2907.

Schulke et al., "The homodimer of prostate-specific membrane antigen is a functional target for cancer therapy", *PNAS*, 2003, 100(22): 12590-12595.

Zuker, Michael, "Mfold web server for nucleic acid folding and hybridization predication", *Nucleic Acids Research*, 2003, 31(13): 3406-3415.

Dollins CM et al. Assembling OX40 aptamers on a molecular scaffold to create a receptor-activating aptamer. Chemistry & Biology. 2008: 8 pp.

Wullner U et al. Cell-specific induction of apoptosis by rationally designed bivalent aptamer-siRNA transcripts silencing eukaryotic elongation factor 2. Current Cancer Drug Targets. 2008; 8(7): 554-565.

Santulli-Marotto S et al. Multivalent RNA aptamers that inhibit CTLA-4 and enhance tumor immunity. Cancer Research. Nov. 1, 2003; 63: 7483-7489.

* cited by examiner

PHARMACEUTICAL COMPOSITIONS FOR HIGH-CAPACITY TARGETED DELIVERY

RELATED APPLICATIONS

This application claims priority to U.S. Provisional Application Ser. No. 61/883,270, filed Sep. 27, 2013, the disclosure of which is incorporated by reference herein in its entirety.

STATEMENT OF GOVERNMENT SUPPORT

This invention was made with government support under grants DOD PCRP 093606 and NIH-NCI P30CA012197. The government has certain rights in this invention.

STATEMENT REGARDING ELECTRONIC FILING OF A SEQUENCE LISTING

A Sequence Listing in ASCII text format, submitted under 37 C.F.R. §1.821, entitled 9151-197_ST25.txt, 2,003 bytes in size, generated on Sep. 25, 2014, and filed via EFS-Web, is provided in lieu of a paper copy. This Sequence Listing is hereby incorporated by reference into the specification for its disclosures.

BACKGROUND

Cell-specific delivery of cytotoxic drugs via passive and active targeting is an important objective in order to improve cancer chemotherapy. Successful targeting may be accomplished if the targeting vehicle has appropriate dimensions for tumor localization via the enhanced permeability and retention (EPR) effect, and binds with high affinity to an antigen that is specifically expressed by targeted cells. The drug complex should also be stable, such that the drug is retained in the complex during targeting, which may take several hours, but released from the complex after binding to the targeted cell. Drug delivery should also be efficient, releasing multiple drugs for each successfully targeted complex. There remains a need for new targeted drug delivery approaches that display stability with high payload delivery in order to accomplish these goals.

BRIEF SUMMARY OF EMBODIMENTS

Provided herein are aptamers and pharmaceutical compositions comprising the same. In some embodiments, the aptamer selectively binds a protein of interest such as an extracellular receptor protein of interest (e.g., a cancer cell extracellular receptor protein, which may be differentially expressed in some embodiments). In some embodiments, the aptamer is directly linked by covalent bonding (e.g., via a geminal diamine linkage) to from 2 to 10 toxin compounds.

In some embodiments, at least one of said toxin compounds is an anthracycline (e.g., doxorubicin, daunorubicin, etc.) or a taxane having a free amine (e.g., paclitaxel, docetaxel, etc.). In some embodiments, the aptamer is directly linked by covalent bonding to said anthracycline or said taxane at a CpG binding site on said aptamer.

In some embodiments, the half life of covalent bonding to the toxin compounds is at least 5 hours, e.g., in human blood plasma or other bodily fluids and/or tissues.

In some embodiments, the aptamer comprises at least one FdUMP.

In some embodiments, the aptamer is provided as a dimeric complex. In some embodiments, the cancer cell extracellular receptor protein is a dimeric protein and said dimeric complex comprises a first nucleic acid that selectively binds to said cancer cell extracellular receptor protein, a second nucleic acid that also selectively binds to said cancer cell extracellular receptor protein, and a linker connecting said first and second nucleic acids. In some embodiments, the dimeric protein is prostate specific membrane antigen (PSMA), transferrin receptor, carbonic anhydrase XII, or an ErbB receptor. In some embodiments, the linker is double-stranded poly-DNA. In some embodiments, the double-stranded poly-DNA comprises at least one CpG binding site.

Also provided herein is a method of selecting an aptamer as described herein that specifically binds to a protein expressed by a cell of interest, wherein in some embodiments the aptamer comprises at least one binding site for one or more active compounds. In some embodiments, primer regions flanking the variable region of the aptamers in the pool contains 1 to 10 mismatches with respect to said forward or reverse primer. In some embodiments, the aptamer so selected has a shorter length than the nucleic acids of said first pool as a result of priming at sites other than the primer regions during amplification (which sites may or may not overlap with the primer region(s), as would be understood by one of skill in the art).

DETAILED DESCRIPTION OF EMBODIMENTS

Figure 1:
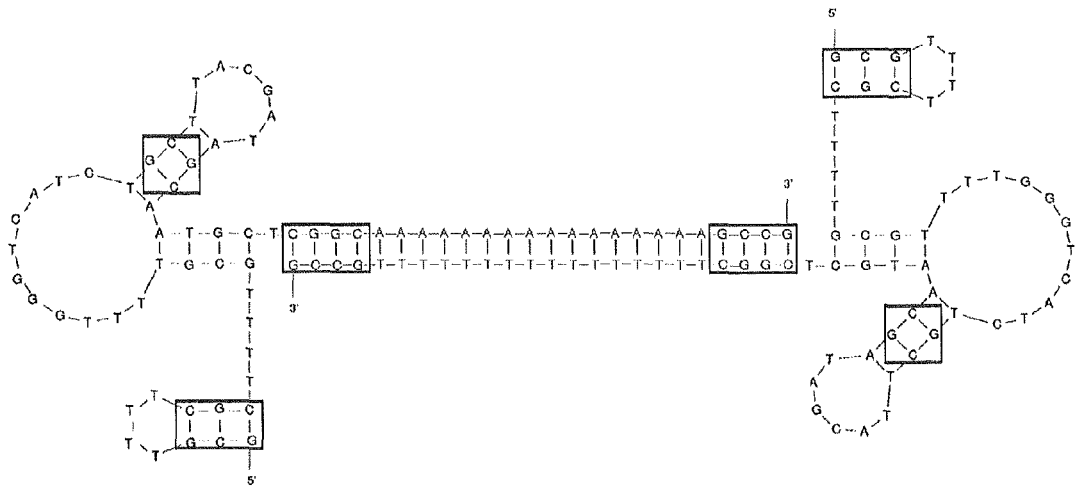
FIG. 1 shows the secondary structure of a dimeric aptamer complex containing CpG sequences appended to the ends of the dA16 (SEQ ID NO:7) or T16 (SEQ ID NO:8), which anneal to form a linker. Boxes indicate potential doxorubicin binding sites.

The present invention is explained in greater detail below. All patent references cited herein are specifically incorporated by reference to the extent they are consistent with the present disclosure. As used in the description of the invention and the appended claims, the singular forms "a", "an" and "the" are intended to include the plural forms as well, unless the context clearly indicates otherwise. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

"Active compound" as used herein includes, but is not limited to, a toxin or cytotoxic agent such as a cytotoxic nucleoside or nucleotide. Other toxins or cytotoxic agents useful as active compounds in the present invention include, but are not limited to, an agent useful as a chemotherapeutic. Examples of active compounds include, but are not limited to, ricin (or more particularly the ricin A chain), aclacinomycin, diphtheria toxin, Monensin, Verrucarin A, Abrin, Tricothecenes, Pseudomonas exotoxin A, taxol, cytochalasin B, gramicidin D, ethidium bromide, emetine, mitomycin, etoposide, tenoposide, anti-mitotic agents such as the vinca alkaloids (e.g., vincristine and vinblastine), colchicin, anthracyclines such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including but not limited to, dactinomycin (formerly actinomycin), bleomycin, mithramycin, calicheamicin, and anthramycin (AMC).

"Cytotoxic nucleoside or nucleotide" as used herein includes, but is not limited to, 2',2'-difluorodeoxycytidine, (dFdC, gemcitabine), 5-fluorouracil (5-FU), 5-fluoro-2'-deoxyuridine-5'-O-monophosphate (FdUMP) or polymeric forms thereof (e.g., FdUMP[9] or FdUMP[10]), 5-fluoro-2'-deoxyuridine (FdU), arabinosylcytosine (Ara-C), arabinosyl adenosine (Ara-A), fluorouracil arabinoside, mercaptopurine riboside, 5-aza-2'-deoxycytidine, arabinosyl 5-azacytosine, 6-azauridine, azaribine, 6-azacytidine, trifluoro-methyl-2'-deoxyuridine, thymidine, thioguanosine, 3-deazautidine, 2-Chloro-2'-deoxyadenosine (2-CdA), AZT (azidothymidine), 2',3'-dideoxyinosine (ddI), cytotoxic nucleoside-corticosteroid phosphodiester, 5-bromodeoxyuridine 5'-methylphosphonate, 5-fluorodeoxyuridine (FdUrd), fludarabine (2-F-ara-AMP), 6-mercaptopurine and 6-thioguanine, 2-chlorodeoxyadenosine (CdA), 2'-deoxycoformycin (pentostatin), 4'-thio-beta-D-arabinofuranosylcytosine, and any other cytotoxic dA, dC, dT, dG, dU, or homologs thereof; or combinations of any of the above. See U.S. Pat. Nos. 5,457,187 (Gmeiner et al.); U.S. Pat. No. 5,614,505 (Gmeiner et al.); U.S. Pat. No. 5,663,321 (Gmeiner et al.); U.S. Pat. No. 5,741,900 (Gmeiner et al.); and U.S. Pat. No. 6,342,485 (Gmeiner).

"Cell of interest" as used herein may be any suitable cell, including, but not limited to, cancer cells, tissue cells (e.g., muscle, bone, nerve, liver, lung, etc.), pathological and non-pathological microbial cells (e.g., bacterial, mycobacterial, spirochetal rickettsial, chlamydial, mycoplasmal, and fungal, etc.), parasitic cells (e.g., protozoal, helminth, etc.), and plant cells, etc.

"Cancer cell" as used herein may be any inappropriately proliferating cell, including, but not limited to, cancerous cells of the lung, colon, ovarian, prostate, bone, nerve, liver, leukemia, and lymphoma, which cells may be malignant or benign.

"Extracellular surface protein" as used herein may be any protein wherein at least a portion of the protein is expressed on the extracellular surface of a cell of interest, including, but not limited to, growth factor receptors, receptor tyrosine kinases, folate hydrolases, GPI-anchored cell surface antigens, pumps, and cell surface receptors including, but not limited to, G-protein coupled receptors, ion channel-linked receptors, and enzyme-linked receptors. In some embodiments, extracellular surface proteins of interest are those "differentially expressed" by upregulation of expression in a targeted cell of interest, in comparison to cells that are not specifically targeted by a cytotoxic nucleotide.

For example, cancer cells differ from normal cells in many respects, including the up- or down-regulation of numerous genes. Among the genes that are differentially expressed and/or regulated in cancer cells are genes that encode proteins that are expressed on the extracellular surface. As an example, specific proteins are expressed on the extracellular surface of prostate cancer (PC) cells that are not expressed (or are expressed at very low levels) by normal prostatic epithelial cells and cells from other normal tissues. Extracellular proteins that are expressed exclusively by PC cells are excellent candidates for specific targeting of malignant cells with anticancer drugs. As an example, the expression of prostate specific membrane antigen (PSMA) is limited to PC cells and cells of the tumor neovasculature (Schulke et al., Proc. Natl. Acad. Sci. USA 100: 12590-12595 (2003)). A second protein that displays characteristics suitable for developing targeted therapeutics for PC is prostate stem cell antigen (PSCA; Saffran et al. 2001, Proc. Natl. Acad. Sci. USA 98: 2658-2663). Other examples of proteins differentially expressed by some cancers are carbonic anhydrases (CA), such as CA IX and CA XI (See U.S. Pat. No. 5,589,579 to Bollon et al.), epidermal growth factor receptor (EGFR, also known as ErbB or HER) (Li et al. 2005, Cancer Cell 7(4):301-311), etc.

"Prostate specific membrane antigen" or "PSMA" is a protein of interest in some embodiments for selective delivery of therapeutics for cancer treatment as a consequence of its elevated expression on the apical plasma membrane of prostate cancer cells (Christiansen et al. 2005, Mol. Cancer Ther. 4: 704-714) and in endothelial cells of vasculature from diverse malignancies. PSMA is expressed by prostate epithelial cells (Gong et al. 1999, Cancer Metastasis Rev. 18: 483-490); however, elevated PSMA expression occurs in advanced prostate cancer (PCa), including bone metastases (Mannweiler et al. 2009, Pathol. Oncol. Res. 15: 167-172) and PSMA expression levels are an independent predictor of PCa recurrence (Perner et al. 2007 Hum. Pathol. 38: 696-701). PSMA is also expressed in vasculature (Liu et al. 1997, Cancer Res. 57: 3629-3634) from many different cancers including a high percentage of bladder (Samplaski et al. 2011, Mod, Pathol. 24: 1521-1529), gastric and colorectal (Haffner et al. 2009, Hum. Pathol. 40: 1754-1761), as well as hepatocellular, renal, breast, and ovarian cancer (Denmeade et al. 2012, Sci Transl Med 4: 140ra86-140ra86). PSMA is expressed as a dimer (Schülke et al. 2003, Proc. Natl. Acad. Sci. U.S.A. 100: 12590-12595), and dimerized ligands targeting the PSMA-dimer display improved activity relative to monovalent ligands (Aggarwal et al. 2006, Cancer Res. 66: 9171-9177).

In some embodiments, extracellular proteins that form dimers are preferred targets. Examples include, but are not limited to, PSMA, transferrin receptor, the zinc enzyme carbonic anhydrase XII (Whittington et al. 2001, PNAS 98(17):9545-9550), ErbB receptors (Zhang et al. 2007, J Clin Invest. 117(8):2051-2058), etc.

In some embodiments, extracellular proteins that are associated with the development of tumor neovasculature are preferred targets. PSMA and vascular endothelial growth factor (VEGF) are non-limiting example thereof.

In accordance with the present disclosure, aptamer targeting of proteins of interest may be particularly beneficial for delivery of chemotherapeutic that are associated with serious systemic toxicities. For example, doxorubicin (or "Dox") is among the most widely-used chemotherapy drugs; however, treatment can result in serious systemic toxicities, such as lethal cardiotoxicity, that may manifest years after treatment.

The A10-3 RNA aptamer, which can target PSMA, has been used to deliver diverse therapeutic modalities selectively to cancer cells, including cisplatin (Dhar et al. 2008, PNAS 105: 17356-17361; Dhar et al. 2011, PNASdoi: 10.1073/pnas.1011379108.), functionalized nanoparticles (Gu et al. 2009, Methods Mol. Biol. 544: 589-598), a micelle-encapsulated PI3K-inhibitor (Zhao et al. 2012, Mol. Pharm. 9: 1705-1716), as well as toxins (Chu et al. 2006, Cancer Res 66: 5989-5992) and siRNA (Ni et al. 2011, J. Clin. Invest. 121: 2383-2390; Dassie et al. 2009, Nat. Biotechnol. 27: 839-849).

However, current RNA aptamers are costly to produce, require modified nucleotides for nuclease stability, and toxins are generally non-covalently associated with the aptamer. Non-covalent complexes of toxins with duplex DNA typically have limited stability, with half-lives of only a few minutes (or less), and it is unlikely that non-covalent complexes of toxins with aptamers would be sufficiently stable for optimal in vivo activity.

Pharmaceutical compositions taught herein may be used for the diagnosis and/or treatment of human subjects, or animal subjects for veterinary or drug development purposes. Examples of animal subjects include mammalian (e.g., dog, cat, mouse, rat, horse, cow, pig, sheep, etc.), reptile, amphibian, and avian (e.g., parrot, budgie, chicken, turkey, duck, geese, quail, pheasant) subjects. "Treat" or "treatment" as used herein refers to an action resulting in a reduction in the severity of a subject's disease or condition, a delay in the progression of the disease or condition, etc.

I. Aptamers and Methods for their Selection

"Aptamer" as used herein refers to a single-stranded nucleic acid (RNA, DNA, or modified forms thereof) whose distinct nucleotide sequence determines the folding of the molecule into a unique three-dimensional structure. Nucleic acid aptamers typically comprise a degenerate or random sequence flanked by fixed sequences onto which primers may bind for amplification. Modified DNA and/or RNA bases may be used or incorporated as desired, e.g., beta-D-Glucosyl-Hydroxymethyluracil. See, e.g., U.S. Pat. No. 7,329,742. The nucleic acids may include any combination of naturally-occurring nucleosides (A, G, C, T, U), and/or nucleoside or nucleotide analogs and/or derivatives as are well known in the art, including cytotoxic, synthetic, rare, non-natural bases or altered nucleotide bases. In addition, a modification can be incorporated to reduce exonucleolytic degradation, such as a reverse (3'→5') linkage at the 3'-terminus.

In some embodiments, aptamers are selected for specific binding to a target of interest such as an extracellular protein as described herein. For such selection, a pool of nucleic acids may be provided from which candidate aptamers are selected. A first pool of nucleic acids may be comprised of range of about $10^6$, $10^8$, $10^{10}$, $10^{11}$, $10^{12}$, or $10^{13}$, to a range of about $10^{14}$, $10^{15}$, $10^{16}$, $10^{18}$, $10^{20}$, $10^{21}$, $10^{22}$, or $10^{23}$ nucleic acid species. In some embodiments, the first pool of nucleic acids comprises about $10^{10}$ to $10^{18}$ nucleic acid species. In some embodiments, the first pool of nucleic acids comprises about $10^{13}$ to $10^{14}$ nucleic acid species. In some embodiments, the first pool of nucleic acids comprises $10^{15}$ nucleic acid species.

The size of the nucleic acid species within the first pool in some embodiments may be in a range of about 30 nucleotides to about 150 nucleotides.

In preferred embodiments, the nucleic acid species of the present invention comprises three regions: a "variable" region flanked on each end by a "primer" regions: Region A and Region B.

The "primer" regions may be used for the annealing of PCR primers during PCR amplification. The two primer regions, A and B, need not be identical to each other, but typically comprise known nucleotide sequences. The lengths of the primer regions can be in a range of about 8 nucleotides to about 35 nucleotides. In some embodiments, the lengths of the primer regions are in a range of about 12 nucleotides to about 22 nucleotides. The length of Region A need not be the same as the length of Region B, and each region may be modified in length and/or sequence based on folding predictions or results following the identification of optimal variable regions.

In some embodiments as taught herein, one or both of the primer regions have "mismatches" with respect to the sequence of the primer intended for use in PCT amplification, i.e., places in the nucleotide sequence where the primer sequence is not complimentary to the primer region of one or more nucleic acid species in the aptamer pool. For example, each of the primers may independently have 1, 2, 3, 4, 5, 6, 7, 8, 9 or 10 mismatches. In some embodiments, use of such mismatches results in an ultimate selected aptamer that is shorter in length than the starting length due to non-specific binding within the aptamer during amplification.

The "variable" region of the nucleic acids species within the first pool typically includes random arrangements of nucleotide sequences. Those variable regions that selectively bind to a target of interest are selected during the selection of a first subpopulation of interest, and may be used in a second pool of nucleic acid species.

In some embodiments, there is a predetermined bias contained within the primer and/or variable regions. The predetermined bias may be used, for example, to facilitate the inclusion of particular cytotoxic nucleotides and/or active compound binding sites. For instance, in some embodiments the first pool of nucleic acids may be biased by including a greater representation of one or more particular nucleosides (A, C, G, T, and/or U). In some embodiments, the nucleic acid pool may include a lesser representation of one or more particular nucleosides (A, C, G, T, and/or U). In some embodiments as taught herein, the pool may include a greater representation of CpG, which are useful as binding sites for covalent attachment. In some embodiments, the nucleic acid pool may include a specific sequence element that may confer antisense or antigene properties to all of the members of the resulting subpopulation.

In some embodiments, the lengths of the nucleic acid species within the first pool includes the "primer" regions, wherein the size of the nucleic acid species can be in a range of about 45 nucleotides to about 130 nucleotides in length. In other embodiments, the size of the nucleic acid species within the first pool can be in a range of about 60 nucleotides to about 100 nucleotides in length. In further embodiments, the size of the nucleic acid species within the first pool can be in a range of about 65 nucleotides to about 80 nucleotides in length. An additional embodiment of the present invention comprises a first pool of nucleic acid species, wherein the size of the nucleic acid species is about 70 nucleotides in length.

In some embodiments, the length of the variable regions within the first pool may be about 10, 15, 20, 25, 30, 35 or 40 nucleotides to about 50, 55, 60, 65, 70, 75, 80, 90, 100, or 105 nucleotides in length, inclusive of any particular length within this range.

The step of selecting a first subpopulation of nucleic acids from the first pool, wherein the first subpopulation comprises at least one nucleic acid that binds specifically to the protein of interest, may be done using any method standard in the art, including, but not limited to, such methods as affinity chromatography, capillary eletrophoresis, field flow fractionation chromatography and surface plasmon resonance. The methods of capillary electrophoresis and field flow fractionation chromatography may be further combined with mass spectrometry to obtain sequence information on the selected first subpopulation of nucleic acids. The step of selecting may be performed once, or the nucleic acids from the first pool may be subjected to additional rounds of selection to identify those nucleic acids with high affinity for the protein target of interest.

Other methods of identifying nucleic acids that can be used as the first nucleic acid herein include, but are not limited to, those described in U.S. Pat. Nos. 7,329,742; 7,312,325; 6,867,289; 6,858,390; and 6,369,208, or variations thereof that will be apparent to those skilled in the art given the present disclosure.

"Amplification" or "amplify" as used herein means the construction of multiple copies of a nucleic acid sequence, or multiple copies complementary to the nucleic acid sequence, using at least one of the nucleic acid sequences as a template. The step of amplifying nucleic acids may be any method standard in the art for amplifying nucleic acids including, but not limited to, polymerase chain reaction (PCR), self-sustained sequence replication, strand-displacement amplification, "branched chain" DNA amplification, ligase chain reaction (LCR) and Q-Beta replicase amplification (QBR). In some embodiments, the selected nucleic acids are amplified using PCR.

In some embodiments, selecting a second subpopulation comprising at least one nucleic acid species from the first subpopulation includes selection of at least one nucleic acid species that is internalized by a cell of interest. Such selection may make use of detection methods such as fluorescence microscopy and flow cytometry, including, but not limited to, fluorescent-activated cell sorting.

To aid in detection, the at least one nucleic acid from the first subpopulation may be labeled with a detectable label using methods standard in the art, wherein the detectable label can include, but is not limited to, fluorescent dyes, fluorophores, chromophores, affinity labels, metal chelates, chemically reactive groups, enzymes, radionuclides, electrochemically detectable moieties, and energy absorbing or energy emitting compounds.

Fluorescent dyes that can be used with the present invention are any capable of binding to nucleic acids as defined herein and include, but are not limited to, the coumarin dyes, acetyl azide, fluorescein isothiocyanate, 1,2-dihexadecanoyl-sn-glycero-3-phosphoethanolamine, 8-(6-aminohexyl)aminoadenosine 3',5'-cyclicmonophosphate, bis(triethylammonium) salt, rhodamine dyes, sulfonyl chloride, CyDye™ fluors, and carboxynaphtofluorescein. The haptenes that may be used for labeling include, but are not limited to, biotin, digoxigenin, and 2,4-dinitrophenyl. The haptenes require fluorescently-labeled antibodies or specific proteins for visualization/detection.

Sequencing at least one selected nucleic acid from a second subpopulation may be done according to methods standard in the art including, but not limited to, automated nucleic acid sequencing procedures as disclosed in Naeve, C. W., (1995) *Biotechniques* 19:448, and sequencing by mass spectrometry. See, e.g., PCT International Publication No. WO 94/16101; Cohen et al., *Adv. Chromatogr.* 36:127-162 (1996); and Griffin et al., *Appl. Biochem. Biotechnol.* 38:147-159 (1993).

Synthesizing a nucleic acid having a sequence corresponding to a selected aptamer may be done according to any method standard in the art including, but not limited to, de novo chemical synthesis of polynucleotides, such as by presently available automated DNA synthesizers, and standard phosphoramidite chemistry. De novo chemical synthesis of a polynucleotide can be conducted using any suitable method, including, but not limited to, the phosphotriester or phosphodiester methods. See Narang et al., *Meth. Enzymol.*, 68:90 (1979); U.S. Pat. No. 4,356,270; Itakura et al., *Ann. Rev. Biochem.*, 53:323-56 (1989); Brown et al., *Meth. Enzymol.*, 68:109 (1979); and U.S. Pat. No. 6,911,310 issued to Heller. For example, automated nucleic acid synthesis may be conducted using an Applied Biosystem 394™ automated DNA/RNA synthesizer (Applied Biosystems, Foster City, Calif.).

II. Incorporation of Active Compounds

In some embodiments, one or more active compounds are incorporated into and/or covalently bound to the aptamer, after and/or during selection.

In some embodiments, the covalent binding comprises a geminal diamine linkage. A "geminal diamine linkage" refers to a group comprising the moiety —NHCRR'NH—, wherein R and R' are each independently hydrogen or alkyl (e.g., C1-C6 alkyl), the moiety having two points of attachment as shown. An illustrative example of a compound having a geminal diamine linkage is the compound N-butyl-N-ethylmethanediamine

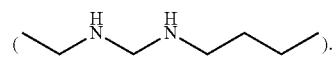

For example, an anthracycline such as doxorubicin may be covalently bound to a CpG site in a nucleic acid such as an aptamer as taught herein with the formation of a Schiff base 1 (e.g., by reaction with formaldehyde). Intercalation of the doxorubicin Schiff base and subsequent reaction of the Schiff base with the 2-amino group of a guanine allows for the formation of a geminal diamine 2, as depicted below in Scheme 1.

Scheme 1.

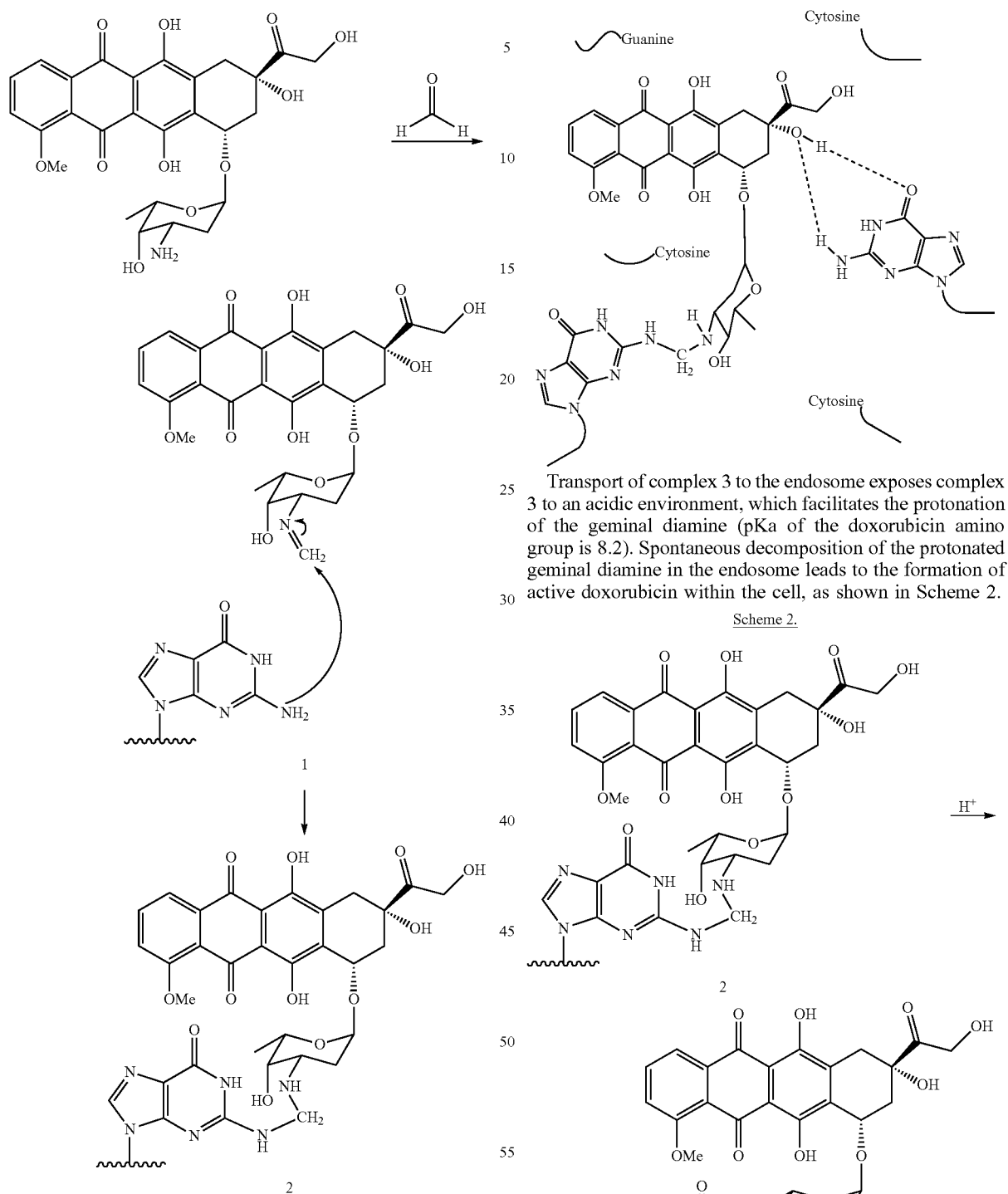

Compound 2 may be further stabilized in the double-stranded nucleic acid by hydrogen bonding of the doxorubicin tertiary alcohol to a second 2-amino group of a deoxyguanosine on the other strand. This complex is depicted below as structure 3. See also Fenick et al. 1997, Doxoform and Daunoform: Anthracycline-Formaldehyde Conjugates Toxic to Resistant Tumor Cell. J. Med. Chem., 40:2452-2461.

Transport of complex 3 to the endosome exposes complex 3 to an acidic environment, which facilitates the protonation of the geminal diamine (pKa of the doxorubicin amino group is 8.2). Spontaneous decomposition of the protonated geminal diamine in the endosome leads to the formation of active doxorubicin within the cell, as shown in Scheme 2.

Scheme 2.

-continued

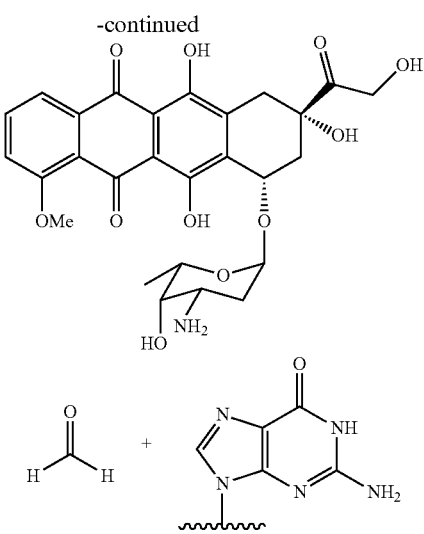

The geminal diamine linkage useful for covalent active compound attachment is readily released under moderately acidic conditions (e.g., pH<6.8, 6,5, 6.2, 6, 5.8, etc.) that typically occur in endosomes following cellular internalization, or possibly in the tumor microenvironment. The active compound so released can diffuse away from the aptamer and effect its therapeutic target, e.g., reacting with host cell DNA.

Further, the reductive activation of an anthracycline such as doxorubicin or daunorubicin can lead to the production of dioxygen species such as superoxide and hydrogen peroxide, which may, in turn, oxidize constituents in the medium to formaldehyde via Fenton chemistry. See, Fenick et al. 1997, J. Med. Chem., 40:2452-2461. Formaldehyde produced in the cell may then react with the anthracycline, and the formed Schiff base can react with host cell DNA.

For example, an active compound such as doxorubicin so released readily translocates to the nucleus and is capable of exerting cytotoxicity to a similar extent as free doxorubicin, which acts via Topoisomerase 2 poisoning. Formaldehyde released from the upon acid-mediated dissociation may promote binding to genomic DNA (Swift et al. 2002, Mol. Cancer Ther. 2: 189-198; Wang et al. 1991, Biochemistry 30: 3812-3815). Thus, formaldehyde is not merely a passive chemical linkage, but may also potentiate genomic DNA binding of an active compound released from the aptamer.

In some embodiments, the active compound may be a taxane, particularly a taxane having a free amine, such as paclitaxel and docetaxel. See Sajjad et al., Applied radiation and Isotopes 70:1624-1631 (2012). Such taxanes may be covalently conjugated to the aptamer in a similar manner as that described above for doxorubicin.

In some embodiments, it is preferred that the selected nucleic acid sequence substantially retains its original three-dimensional structure of the native sequence following the incorporation of the active compounds. Folding calculations may be performed to compare the predicted folding patterns of the chemical structure of the native nucleic acid sequence with that of a nucleic acid sequence incorporating one or more active compounds. Calculations can be performed with, e.g., folding programs such as mFOLD (Michael Zuker, Burnet Institute). Such calculations apply an algorithm to the native sequence of the nucleic acid to determine folding patterns that yield the most stable secondary structures. This approach provides insight into the likely location of double helical regions that occur within the three-dimensional structure of the nucleic acid. The structural characteristics of the native and modified nucleic acids can also be determined using circular dichroism (CD) spectroscopy and ultraviolet (UV) hyperchromicity measurements. Other methods of comparison will be apparent to those skilled in the art. In some embodiments, preferred nucleic acids of interest are those that incorporate compounds of interest in such a way as to not significantly or unduly alter the folding characteristics and/or ultimate three-dimensional structure of the native sequences.

In some embodiments, aptamers incorporating one or more active compounds may be further evaluated for the extent to which they selectively kill cells of interest, e.g., through the release of cytotoxic nucleotides by 3'-O-exonucleolytic degradation. Cell viability can be evaluated, e.g., using 3-(4,5-dimethythiazole-2-yl)-5-(3-carboxymethoxyphenyl)-2-(4-sulfophenyl)-2H-tetrazolium, inner salt (MTS) assays. Preferred nucleic acids are those that are cytotoxic towards cells of interest and not cytotoxic to non-targeted cells.

III. Dimeric Aptamers

In general, "dimeric" aptamers as described herein are compounds of the general formula A-B-C, wherein:

A is a first aptamer that specifically binds to or targets an extracellular surface protein of interest, B is a linker (e.g., nucleic acid linker and/or alkyl linker, etc.); and C is a second apatmer that specifically binds to or targets an extracellular surface protein of interest, which aptamer can be the same as, or different from, the first aptamer A, and/or specifically binds or targets the same or a different protein of interest.

An "alkyl linker" or "alkyl spacer," used interchangeably herein, may, for example, be a partially saturated or fully saturated C2, C3, C4, or C5, to C6, C7, C8, C9 or C10 alkyl group, which group may be linear or branched. The linker may be of any suitable length, for example, 10, 20 or 50 Angstroms in length, up to 100, 200 or 500 Angstroms in length, or more, considering the targets of aptamer A and aptamer B and how they are expressed and/or dimerized by a cell of interest.

A "nucleic acid linker" or "nucleic acid spacer," used interchangeably herein, may be any suitable nucleic acid, and in some embodiments is double stranded in whole or in part in the formed dimeric aptamer (see, e.g., FIG. 1). In some embodiments, the nucleic acid linker is provided by hybridizing complimentary ends of each of the two apatmers in the dimeric pair. In some embodiments, the nucleic acid linker may be a poly-T/poly-A linker (optionally with some or all of the poly-T replaced by poly-FdU). In some embodiments, the nucleic acid linker may include one or more CpG binding sites useful for covalent binding of an active compound as taught herein.

One or more alkyl linker(s) may also be included within the nucleic acid linker, which in some embodiments provides flexibility (e.g., rotational flexibility) of the complex, which may result in a higher binding affinity. See also, U.S. Patent. Application Publication No. 2010/0261781 to Gmeiner.

In some embodiments, a double-stranded nucleic acid spacer has a sequence that is sufficiently thermally stable such that the dimeric aptamer remains dimeric under physiological conditions (e.g., having a melting temperature of at least 35, 37, 40, 45, 50, 55, 60, or 65 degrees Celsius in a solution isotonic with blood or other tissues), preferably for times sufficient for the dimeric aptamers to localize specifically to targets in vivo, considering the formulation and/or route of administration.

IV. Formulations and Routes of Administration

The aptamers as taught herein may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the aptamer may be admixed with, inter alia, an acceptable carrier. The carrier must, of course, be acceptable in the sense of being compatible with any other ingredients in the formulation and must not be unduly deleterious to the patient. The carrier may be a solid or a liquid, or both, and is preferably formulated as a unit-dose formulation with respect to the aptamer and/or active compound payload, for example, a tablet, which may contain from 0.01 or 0.5% to 95% or 99% by weight of the active compound(s).

Formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, inclusive of intra-tumoral administration, although the most suitable route in any given case will depend on the nature and severity of the condition being treated and on the nature of the particular active compound being used.

Formulations suitable for oral administration may be presented in discrete units, such as capsules, cachets, lozenges, or tablets, each containing a predetermined amount of the aptamer and/or active compound(s); as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an aptamer and/or active compound(s) in a unit dosage form in a sealed container. The aptamer and/or active compound(s) may be provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the active compound(s). When the active compound(s) is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

The present invention is further exemplified by the following non-limiting examples.

EXAMPLES

A new strategy was developed for improved targeted delivery of doxorubicin (Dox) to PSMA+ cancer cells using a novel dimeric DNA aptamer complex bound to Dox through a pH-sensitive linker. PSMA is expressed on the plasma membrane as a dimer, and dimerized ligands targeting PSMA display improved activity relative to monovalent ligands (Aggarwal et al. 2006, Cancer Res. 66: 9171-9177). Dimeric aptamer complex (DAC) take advantage of the dimeric nature of PSMA.

5'-dCpG, the preferred binding site for Dox, was interspersed in the primers used for PCR amplification during SELEX to permit Dox-binding motifs to be retained in the final DNA aptamer sequence (FIG. 1). Priming sequences were imperfectly matched to fixed sequences within the template, permitting aptamer length to vary during the selection process.

Identified was a 48-nucleotide DNA aptamer (SZTI01) using an affinity matrix consisting of the extracellular domain of human PSMA.

Results

Thermal Stability of Dimeric Aptamer Complexes. A duplex DNA "bridge" was used to link the two DNA aptamers in the DAC (FIG. 1). The bridging DNA duplex was designed to be sufficiently thermally stable such that the dimeric aptamer complex (DAC) remains intact under physiological conditions for times sufficient for aptamers to localize specifically to targets in vivo, and includes a preferred site for Dox binding (CpG). The fixed sequences used during the aptamer selection process also included preferred sites for Dox binding that are included in the final DAC structure.

Figure 2:
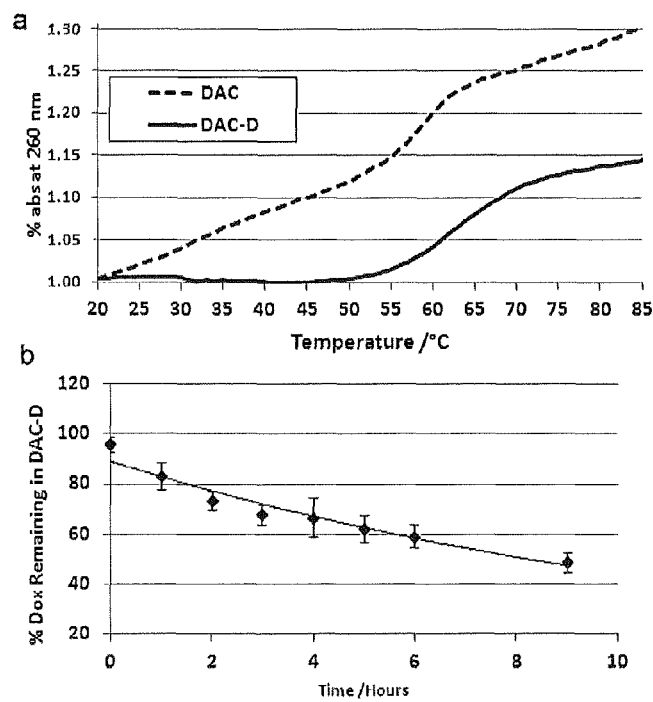
FIG. 2 presents a physical characterization of DAC and DAC-D. (a) The melting temperature (Tm) of DAC and DAC-D was determined by measuring the ultraviolet absorbance at 260 nm and by heating the samples at 0.7° C./minute. (b) Dox fluorescence was measured by exciting the sample with a 532 nm laser and reading the emission at 580 nm. The calculated half-life of transfer from DAC-D was found to be 8.27 hours. Error bars represent mean±SD. DAC, dimeric aptamer complex; DAC-D, dimeric aptamer complex with doxorubicin.

Thermal melting profiles were obtained for DACs with and without Dox modification to evaluate stability of these complexes and any effects Dox may have on thermal stability (FIG. 2). The temperature-dependent UV melting profile for the dA16:T16 DAC indicated some reduction in secondary structure at temperatures less than 30° C. with initial dissociation of the dimeric complex at ~41° C. with a dissociation temperature of ~47° C. While dissociation for this dimeric complex occurred above physiological temperature, increased stability was desired to promote long-term stability under physiological conditions. Further, the A-T duplex used to form this dimeric complex did not include a Dox-binding sequence motif.

To address these issues, an alternative dimeric aptamer complex (DAC) was prepared by appending GCCG and CGGC sequences to the 5'- and 3'-ends of the A16:T16 DNA duplex forming sequences (FIG. 1). The resulting DAC displayed a dissociation temperature of ~58° C., thus displaying stability suitable for further development. Covalent modification of DAC with Dox (DAC-D) further enhanced complex stability, and the DAC-D complex displayed minimal change in absorbance for temperatures lower than the Tm consistent with Dox stabilizing DAC structure (FIG. 2a).

The secondary structure and thermal stability of DAC were further investigated using CD spectroscopy. The DAC complexes displayed CD spectra typical of B-form DNA with a maximum at 283 and a minimum at 248 nm consistent with the tail-forming sequences forming the target structures. Covalent modification with Dox in the DAC-D complex has no discernible effect on overall secondary structure for the complex although a slight sharpening in the peaks was noted. The DAC-D complex displayed less sensitivity to increased temperature relative to DAC and DAC+Dox, indicating that covalent modification with Dox stabilizes the overall complex.

Formation and Dissociation of Covalent Dox-Conjugates. The duplex DNA binding motif stabilizing the DAC has the potential for binding two equivalents of Dox per complex. In addition, the DNA aptamers comprising the complex contained other CpG sites for potential Dox binding (FIG. 1). A covalent complex was formed between the DAC and Dox (DAC-D) by mixing the dimeric complex with a four-fold excess of Dox in the presence of formaldehyde. Covalent linkages were formed at 4:1 stoichiometry (Table 1), and Dox transfer from the resulting covalent complex (DAC-D) was evaluated in which Dox fluorescence is effectively quenched, to an excess of a 25mer DNA hairpin in which Dox fluorescence is less effectively quenched. These studies revealed the half-life for Dox covalently bound in DAC-D via formaldehyde was >8 h (FIG. 2b). In contrast, the dissociation of the non-covalent complex was too rapid to measure using this assay, but is fully dissociated in ≤5 minutes. These studies indicated that covalent attachment of Dox results in formation of a complex with greatly increased retention of Dox that is well-suited for drug delivery applications in vivo.

TABLE 1

Absorbance values for DAC-D complexes of different aptamer:Dox ratio.

|  | Abs at 498 nm | Abs at 260 nm | Dox Conc (μM) | DNA Conc (μM) | Dox:DNA |
|---|---|---|---|---|---|
| DAC-D 1 | 0.0358 | 1.0223 | 3.48 | 0.793 | 4.388398 |
| DAC-D 2 | 0.0272 | 1.0084 | 2.85 | 0.768 | 3.710938 |
| DAC-D 3 | 0.0376 | 1.61 | 4.02 | 1.19 | 3.378151 |
| avg |  |  |  |  | 3.825829 |
| std dev |  |  |  |  | 0.51483 |

Figure 3:
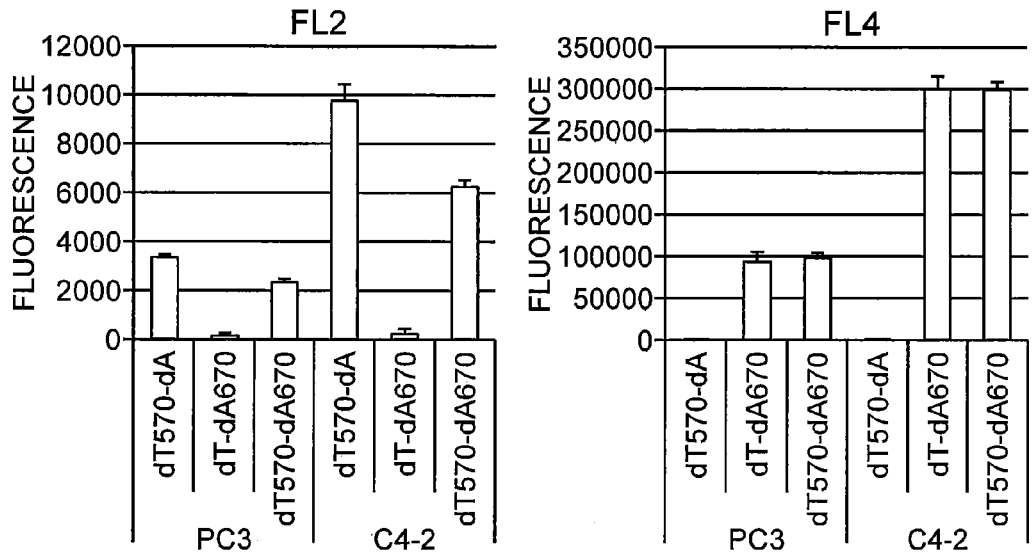
FIG. 3 presents flow cytometry data. Cells were incubated with DAC for two hours before measuring the amount of fluorescence emitted by either Quasar 670 or Quasar 570 as a readout for aptamer internalization.

PSMA-Specific Uptake of Dimeric Complexes. The selective delivery of Dox to PSMA+ cells requires binding and ideally internalization of the complex. To evaluate to what extent the DAC was specific for binding and internalization into PSMA+ cells, internalization of the complex in PSMA+ C4-2 cells and PSMA-null PC3 cells was compared using confocal microscopy and flow cytometry. The component of the dimeric complex containing dA16 ssDNA was labeled with Quasar 570 while the component with T16 ssDNA was labeled with Quasar 670, permitting simultaneous detection and visualization of each aptamer component. Confocal microscopy revealed minimal uptake of either fluorescently-labeled aptamer into PC3 cells; however strong signal was observed for each fluorescent aptamer signal in PSMA+ C4-2 cells. Further, fluorescence emitted from each of the two aptamers was completely co-localized consistent with uptake and retention of the DAC in dimeric form. Fluorescence emitted from the aptamer complexes appeared punctate, with nuclear exclusion, consistent with endosomal localization of the DAC, which was confirmed by co-localization with the endosomal marker FITC-dextran. Flow cytometry also confirmed specificity of DAC for PSMA+ C4-2 cells (FIG. 3). Pre-incubation of C4-2 cells with J591 PSMA-specific monoclonal antibody attenuated DAC uptake consistent with PSMA-specific internalization.

PSMA-Specific Delivery of Dox. The serious toxicities associated with Dox treatment indicate that premature release of Dox from targeting vehicles is likely to be therapeutically detrimental. In this regard, non-covalent complexes of Dox with DNA have demonstrated improved toxicity profiles relative to free Dox (Trouet and Jollés 1984, Semin. Oncol. 11: 64-72); however covalent linkage of Dox with a targeted DNA-vehicle should markedly enhance efficacy and reduce systemic toxicities by limiting Dox-dissociation while in circulation.

A strategy was developed to covalently attach Dox to the DAC using formaldehyde, a method previously shown to promote covalent complex formation of Dox with genomic DNA (Zeman et al. 1998, Proc Natl Acad Sci USA 95: 11561-11565), The specific delivery of Dox to PSMA+ cells using DAC-D was evaluated using confocal microscopy. While non-complexed Dox readily accumulated in the nuclei of both PC3 and C4-2 cells, Dox delivered using DAC-D internalized nearly exclusively into C4-2 cells with minimal accumulation in PC3 cells. Dox fluorescence was exclusively nuclear, while the aptamer fluorescent signal from DAC-D displayed nuclear exclusion consistent with Dox becoming dissociated from the DAC-D following cellular internalization.

These results are consistent with Dox becoming dissociated in the acidic environment of the endosome following cell-uptake of DAC-D followed by nuclear localization of Dox. The results thus confirm PSMA-specific uptake of the DAC-D complex with nuclear delivery of Dox.

Figure 4:
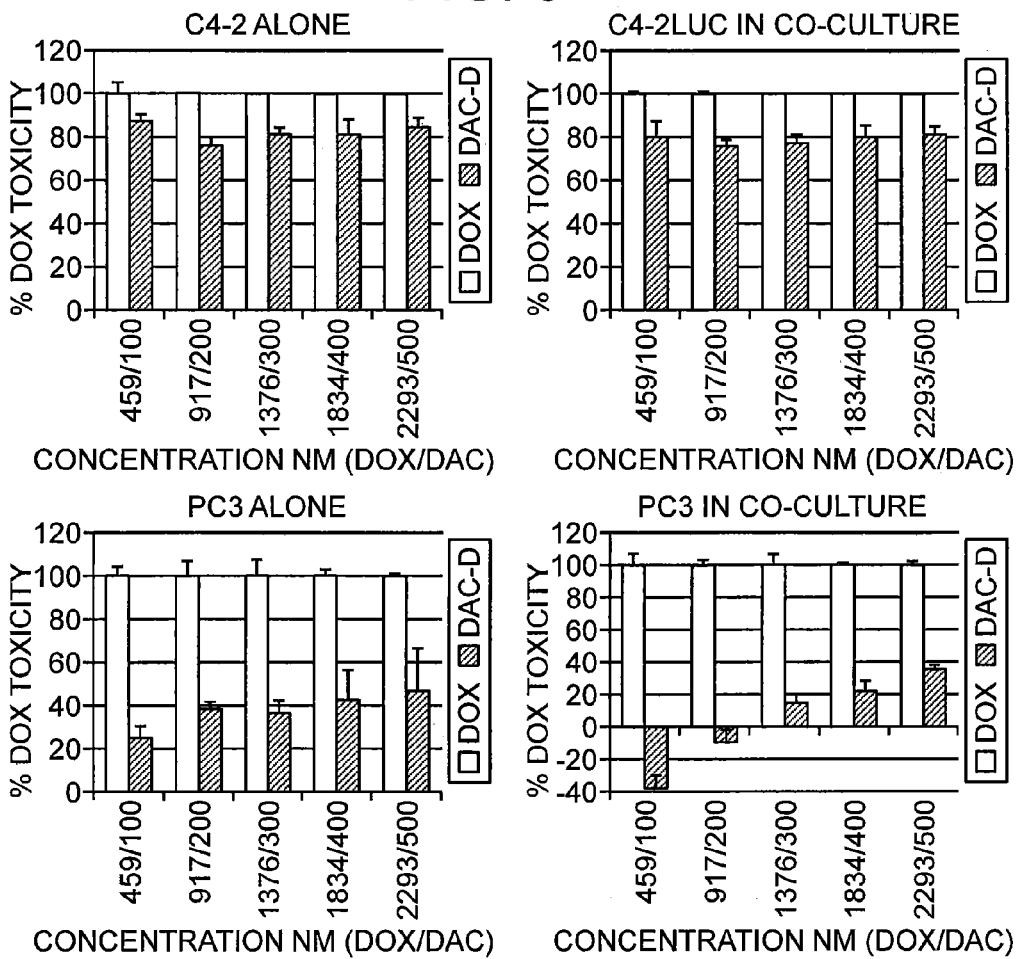
FIG. 4 presents the results of treatment of cell cultures with the dimeric toxin-loaded construct, DAC-D. PC3 and C4-2 cells were incubated alone or in coculture and were treated with DAC-D, DAC+Dox, or free-Dox for 24 hours. Media was replaced and cells were allowed to grow for 48 hours before determining viability. Percentage of Dox retained was found by comparing the viability of DAC-D (or DAC+Dox) with Dox. There is no statistical difference between C4-2 cells alone versus C4-2 cells in coculture, however there is a significant reduction in cytotoxicity for PC3 cells in coculture versus PC3 cells alone (P<0.05). Error bars represent mean±SEM. DAC, dimeric aptamer complex; DAC-D, dimeric aptamer complex with doxorubicin; Dox, doxorubicin.

PSMA-Dependent Selective Cytotoxicity. The specificity of DAC-D for PSMA+ cells was evaluated using cell-viability assays in PC3 and C4-2 cells. The results are shown in FIG. 4. Free-Dox was highly cytotoxic to both PC3 and C4-2 cells consistent with the wide-spectrum activity previously reported. In contrast, Dox delivery via DAC-D was highly cytotoxic towards C4-2 cells, but displayed greatly reduced cytotoxicity to PC3 cells. For example, at Dox concentrations that resulted in ~90% reduction in viability for free-Dox (2 µM), the same amount of Dox delivered via DAC-D displayed greater than 80% potency towards targeted C4-2 cells and less than 50% of cytotoxic activity towards PC3 cells.

An especially challenging situation for targeted drug delivery occurs when targeted cells are in close proximity to non-malignant cells as arises in metastases to vital organs. In this case, highly localized cytotoxicity is desirable. To simulate this challenging environment, we performed co-culture of luciferase-transfected C4-2 cells (C4-2-luc) with PC3 cells and assessed the viability of each cell line in co-culture independently (FIG. 4). Preliminary studies demonstrated that C4-2-luc and C4-2 cells displayed no significant difference in viability in response to Dox or the DAC-D complex. The response of C4-2-luc cells in co-culture with PC3 cells was similar to C4-2 cells in mono-culture with DAC-D retaining greater than 80% cytotoxicity in the mixed environment. In contrast, PC3 cells in co-culture with C4-2-luc cells showed markedly decreased response to DAC-D relative to studies in monoculture ($p<0.05$). The results are consistent with the DAC-D undergoing selective internalization into targeted PSMA+ C4-2 cells, reducing the DAC-D available for non-specific uptake into non-targeted PC3 cells.

Discussion

Aptamer-mediated delivery is a promising technology for improving the therapeutic index of cytotoxic drugs that cause serious systemic toxicities, such as Dox. A new DNA aptamer to PSMA was identified and developed a dimeric aptamer complex (DAC) to take advantage of PSMA being expressed as a dimer. The objective was to use the DAC as a scaffold for high-capacity drug delivery. The process used for aptamer identification was designed to identify DNA sequences that included preferred Dox binding sites (e.g., 5'-CpG). Also developed was a process for covalent modification at the preferred binding sites with Dox resulting in a high capacity (4:1) payload. The covalent linkage utilized is pH-sensitive releasing free Dox in the acidic environment of endosomes following internalization into targeted cells. Released Dox migrates to the nucleus and binds genomic DNA interfering in replication and mitosis while the DAC is retained in the cytosol. The resultant DAC-D complex is internalized selectively into PSMA+ cells and is highly cytotoxic to these cells while displaying minimal effects to PSMA-null cells. This high degree of selectivity is retained in the context of co-culture experiments in which PSMA+ cells retain full sensitivity to the targeted complex even while co-cultured adjacent PSMA-null cells are not affected. Based on these data, it is expected that DAC-D complexes will be highly effective anti-tumor agents in vivo with minimal systemic toxicity.

Dimeric aptamer complexes have potential advantages relative to monomeric aptamers for drug delivery applications in terms of target selection, target avidity, physical and chemical stability, higher payload capacity, improved pharmacokinetics, and utility if partly damaged, among other properties. The present studies utilized a DAC with both components targeting PSMA which is expressed as a dimer.

The length of the 24 base pair DNA duplex connecting the component aptamers is approximately 70 Å, which is similar to the dimensions of the PSMA dimer, making it possible for the component aptamers to bind simultaneously, although optimization of DAC dimensions would be required to fully optimize simultaneous binding. The structure of the DAC utilized in the present studies was stable under physiologically relevant conditions and useful for high-capacity drug delivery with a 4:1 stoichiometry payload. In principle, additional Dox binding sites can be included into the structure to further enhance drug-delivery potential.

The chemical linkage used for covalent Dox attachment enables convenient synthesis with high yields and straightforward purification. While this approach is readily scaled for in vivo studies and eventual clinical applications, one of the more important advantages of using this chemistry for Dox delivery, in particular, is that Dox is readily released from the DAC-D under moderately acidic conditions (pH<6) that occur in endosomes following cellular internalization, or possibly in the tumor microenvironment. Dox released from endocytic DACs readily translocates to the nucleus and is capable of exerting cytotoxicity to a similar extent as free Dox which acts via Topoisomerase 2 poisoning. Formaldehyde released from the DAC-D upon acid-mediated dissociation has the potential to promote Dox binding to genomic DNA (Swift et al. 2002, Mol. Cancer Ther. 2: 189-198; Wang et al. 1991, Biochemistry 30: 3812-3815.). Thus, formaldehyde is not merely a passive chemical linkage, but may also potentiate genomic DNA binding of Dox released from the DAC-D delivery vehicle. This approach has advantages relative to strategies that use covalent linkers that lack this potential for enhancing genomic DNA binding by released Dox.

The DAC-D described here has molecular weight (~45 kDa) suitable for prolonged retention in plasma as well as tumor localization via the EPR and with specificity for malignant cells via PSMA targeting. Ultimately, DAC-D should prove useful for clinical management of cancer.

Material and Methods

DNA SELEX. Recombinant human PSMA extracellular domain (720 amino acids) was expressed from baculovirus (Kinakeet Biotechnology; Richmond, Va.). The recombinant protein included a His-tag sequence that was used to form an affinity matrix using Talon beads which was then used in a DNA SELEX procedure to identify DNA aptamers to PSMA. DNA aptamers were selected from a library including a 47 nucleotide random sequence flanked by fixed sequences of 21 nucleotides each. The fixed sequences selected permit formation of short hairpins in the final aptamer that include stem regions with sequence elements favorable for Dox binding (underlined). The sequence for the random library was:

```
                                        (SEQ ID NO: 1)
dGCGAAAACGCAAAAGCGAAAA(N47)ACAGCAATCGTATGCTTAGCA
```

Initially 8 µg ssDNA from the random library (307 picomoles of DNA; 186 trillion sequences) was converted to dsDNA using a T7 fill-in reaction and amplified by PCR using primers that were imperfectly matched to the template.

```
                                        (SEQ ID NO: 2)
    5' dGCGTTTTCGCTTTTGCGTTTT (forward)

(SEQ ID NO: 3)
    5' dAGCATTGCTATCGTAAGCAGA (reverse)
```

The 5'-primer was synthesized with a 5'-phosphate and the resulting dsDNA was converted to ssDNA using λ-exonuclease to selectively cleave the strand amplified with the phosphorylated primer. SELEX forward rounds were performed by adding 1 mg of PSMA bound to Dynabeads Talon to 700 μL of binding buffer (100 mM NaCl, 20 mM Tris, 2 mM MgCl2, 5 mM KCl, 1 mM CaCl2, 0.2% Tween-20, pH 8). The beads were removed using a Dynal magnet and were washed four times with binding buffer. At least 10 μg of ssDNA was annealed by heating to 95° C. followed by gentle cooling and was added to the PSMA-matrix followed by vortexing and incubation for 1 h at 37° C. with mild agitation. The supernatant was removed and 20 μL of 5 μM 5'-phosphorylated primer was added to the beads and the mixture was heated to 95° C. for 5 min following which the beads were sequestered and the supernatant transferred to a clean microfuge tube and DNA converted to dsDNA using a primer-extension reaction using T7 polymerase. DNA was collected by ethanol precipitation and then amplified by 10 cycles of PCR using a phosphorylated 3'-primer. The dsDNA was purified by gel electrophoresis followed by ethanol precipitation and then converted to ssDNA by treating 32-40 μg of dsDNA with λ-exonuclease for 30 min at 37° C. followed by ethanol precipitation. The resulting ssDNA was analyzed by gel electrophoresis and quantified by UV absorbance and used in a subsequent SELEX forward or counter round. Counter rounds differed from forward rounds by incubation with a magnetic bead matrix that did not contain PSMA and using the DNA that did not bind to the matrix for subsequent PCR amplification. A total of 10 forward and two counter rounds were performed. After the final SELEX round, ssDNA was converted to dsDNA using a T7 fill-in procedure and was cloned into a pGEM vector (Promega) for sequencing. A single, 48 nucleotide sequence (SZTI01) was identified and used in subsequent studies.

SZTI$_{01}$:
(SEQ ID NO: 4)
dGCGTTTTCGCTTTTGCGTTTTGGGTCATCTGCTTACGATAGCAATGCT

PSMA-Specific Aptamer Synthesis: The DNA aptamer sequences were synthesized at either the University of Calgary (Calgary, Canada) or IDT Inc. (Coralville, Iowa). Aptamers were reconstituted in sterile, nuclease-free H$_2$O at 100 μM. Dimeric aptamer complexes were prepared from aptamers that included either a dA16 or T16 single-stranded tail at the 3'-terminus (dA16:T16DAC) by mixing the 2 monomers at 1:1 ratio followed by heating to 95° C. and gentle cooling. The DAC used for these studies (unless otherwise indicated) included the sequences dCGGCA16GCCG (SEQ ID NO:5) or dCGGCT16GCCG (SEQ ID NO:6). The secondary structure for the DAC calculated using m-fold is shown in FIG. 1.

Synthesis of DAC-D Complexes: The covalent complex of DAC with Dox (DAC-D) was prepared by mixing 250 μL of a 50 μM solution of the DAC with a Dox-formaldehyde solution prepared upon incubation of a 0.37% formaldehyde solution in Dulbecco's Phosphate Buffered Saline without Calcium or Magnesium (DPBS) pH 7.4 with Dox. The reaction proceeded in a light-free manner at 4° C. for 48 hours. The solution was extracted once with 300 μL of phenol:chloroform followed by two additional extractions with 300 μL chloroform, The aqueous phase was then ethanol-precipitated and the pellet rinsed 2× with 70% ethanol and once with absolute ethanol and dried under reduced pressure. The red pellet was re-suspended in 100 μL dH$_2$O, Yields were typically >90% based on DNA recovery.

Determination of Dox:DNA Ratios: DNA samples were prepared in dH$_2$O, and absorbencies were measured from 200-800 nm using a Beckman Coulter DU800 spectrophotometer. A standard curve of Dox was established between 1 μM and 10 μM by using absorbencies at 494 nm at 85° C. To assess the amount of Dox covalently bound to DNA, the samples were heated to 85° C. before measuring the absorbance at 494 nm and 260 nm. The 260 nm wavelength was used to determine the DNA content in the sample and to determine the Dox:DNA ratio.

Dox Transfer from DAC-D: Samples of DAC-D, or the non-covalent complex (DAC+D) or free Dox 625 nM were prepared in DPBS with or without a 100-fold (by weight) excess of a 25mer DNA and were incubated at 37° C. Changes in fluorescence intensity were determined using a Typhoon-9210 variable mode imager with excitation set to 532 nm and the emission filter at 580 nm.

Temperature-Dependent UV Studies: Temperature-dependent UV absorption spectra were obtained using a Beckman Coulter DU-800 UV-Vis spectrophotometer, Samples of DAC, DAC-D, and DAC+D were prepared. The temperature was increased at a rate of 0.7° C./min over the range 20-85° C. and absorbance at 260 nm was measured for each sample, (400 μL, 1 μM) concentration.

Cell lines: The C4-2 cell line was a gift from Dr. Elizabeth M. Wilson (UNC, Chapel Hill, N.C.). C4-2Luc cell line was generated by transfecting C4-2 cells with pTRE2hygro and firefly luciferase (PGL3). PC3 cells were purchased from cell and viral vector core laboratory at Wake Forest School of Medicine. All cells were maintained with RPMI 1640 (Gibco, Grand island, N.Y.) with 10% fetal bovine serum (Gemini Bio-Products, West Sacramento, Calif.). All cells were kept at 5% CO$_2$ at 37° C.

Confocal microscopy: Cells were seeded at 20,000 cells/well in 8-well Lab-Tek® II chambered #1.5 German coverglass system (Thermo Fisher Sci., Waltham, Mass.), and incubated at 37° C. under 5% CO$_2$ for 2 days. Cells were incubated with 1 μM of DAC in which the dA16 aptamer was labeled with Quasar 570 at the 5'-terminus and the T16 aptamer was labeled with Quasar 670 dyes in RPMI with 10% FBS for 2 h at 37° C. Cells were washed with fresh media and DPBS, followed by a 5 min fixation with 3.7% formaldehyde in DPBS. Cells were visualized using a Zeiss LSM510 confocal microscope (Carl Zeiss, Oberkochen, Germany). Cells were also incubated with 1 μM of DAC-D (or the non-covalent DAC+D), for 2 h. DAC were only labeled with Quasar 670 for these studies as the Quasar 570 emission would interfere with the Dox emission. Cells were washed, fixed, and imaged using identical procedures.

Flow cytometry: PC3 and C4-2 cells were incubated with 1 μM of DAC for 2 h at 37° C. Dimers were fluorescently labeled with either Quasar 570 or 670 alone, or both. Cells were trypsinized and washed with PBS twice. Cells re-suspended in PBS were analyzed to measure their intracellular fluorescence using the Accuri™ C6 flow cytometer (BD Biosciences).

Cytotoxicity measurements: PC3, C4-2, and C4-2Luc cells were seeded at a density of 3,000 cells/well in 96-well plates and incubated at 37° C. under 5% CO$_2$. Next day, the cells were treated with Dox, DAC+Dox, or DAC-D for 24 h. Next day the treatment was removed, cells were washed once with warm fresh media and incubated for another 48 h in fresh media. Cell counts were measured indirectly by measuring the ATP amounts using CellTiter-Glo® luminescent cell viability assay (Promega, Madison, Wis.) according to the manufacturer's protocol. In co-culture experiments, PC3 and C4-2Luc cells were each seeded at a density of 1,500 cells/well in 96-well plates. Co-cultured cells were treated with Dox, DAC+Dox, or DAC-D and cell viability was also measured using the CellTiter-Glo® assay. Luciferase levels were measured for co-cultures of PC3 and C4-2Luc cells using a luciferase reporter assay system (Promega). PC3 and C4-2Luc cells were seeded and treated as described above and the cells were lysed and luciferase activity was measured according to the manufacturer's protocol.

REFERENCES CITED

1. Maeda, H (2012). Macromolecular therapeutics in cancer treatment: The EPR effect and beyond. Journal of Controlled Release 164: 138-144.
2. Byrne, J D, Betancourt, T and Brannon-Peppas, L (2008). Active targeting schemes for nanoparticle systems in cancer therapeutics. Adv. Drug Deliv. Rev. 60: 1615-1626.
3. Li, L, Sun, J, He, Z (2013). Deep penetration of nanoparticulate drug delivery systems into tumors: Challenges and Solutions. Curr. Med. Chem. In Press.
4. Erickson, H P (2009). Size and shape of protein molecules at the nanometer level determined by sedimentation, gel filtration, and electron microscopy. Biol Proced Online 11: 32-51.
5. Christiansen, J J, Rajasekaran, S A, Inge, L, Cheng, L, Anilkumar, G, Bander, N H, et al. (2005). N-glycosylation and microtubule integrity are involved in apical targeting of prostate-specific membrane antigen: implications for immunotherapy. Mol. Cancer Ther. 4: 704-714.
6. Denmeade, S R, Mhaka, A M, Rosen, D M, Brennen, W N, Dalrymple, S, Dach, I, et al. (2012). Engineering a Prostate-Specific Membrane Antigen—Activated Tumor Endothelial Cell Prodrug for Cancer Therapy. Sci Transl Med 4: 140ra86-140ra86.
7. Rajasekaran, S A, Christiansen, J J, Schmid, I, Oshima, E, Ryazantsev, S, Sakamoto, K, et al. (2008). Prostate-specific membrane antigen associates with anaphase-promoting complex and induces chromosomal instability. Mol. Cancer Ther. 7: 2142-2151.
8. Gong, M C, Chang, S S, Sadelain, M, Bander, N H and Heston, W D (1999). Prostate-specific membrane antigen (PSMA)-specific monoclonal antibodies in the treatment of prostate and other cancers. Cancer Metastasis Rev. 18: 483-490.
9. Mannweiler, S, Amersdorfer, P, Trajanoski, S, Terrett, J A, King, D and Mehes, G (2009). Heterogeneity of prostate-specific membrane antigen (PSMA) expression in prostate carcinoma with distant metastasis. Pathol. Oncol. Res. 15: 167-172.
10. Perner, S, Hofer, M D, Kim, R, Shah, R B, Li, H, Möller, P, et al. (2007). Prostate-specific membrane antigen expression as a predictor of prostate cancer progression. Hum. Pathol. 38: 696-701.
11. Liu, H, Moy, P, Kim, S, Xia, Y, Rajasekaran, A, Navarro, V, et al. (1997). Monoclonal antibodies to the extracellular domain of prostate-specific membrane antigen also react with tumor vascular endothelium. Cancer Res. 57: 3629-3634.
12. Samplaski, M K, Heston, W, Elson, P, Magi-Galluzzi, C and Hansel, D E (2011). Folate hydrolase (prostate-specific membrane [corrected] antigen) 1 expression in bladder cancer subtypes and associated tumor neovasculature. Mod. Pathol. 24: 1521-1529.
13. Haffner, M C, Kronberger, I E, Ross, J S, Sheehan, C E, Zitt, M, Mühlmann, G, et al, (2009). Prostate-specific membrane antigen expression in the neovasculature of gastric and colorectal cancers. Hum. Pathol. 40: 1754-1761.
14. Schülke, N, Varlamova, O A, Donovan, G P, Ma, D, Gardner, J P, Morrissey, D M, et al. (2003). The homodimer of prostate-specific membrane antigen is a functional target for cancer therapy. Proc. Natl. Acad. Sci. U.S.A. 100: 12590-12595.
15. Aggarwal, S, Singh, P, Topaloglu, O, Isaacs, J T and Denmeade, S R (2006). A dimeric peptide that binds selectively to prostate-specific membrane antigen and inhibits its enzymatic activity. Cancer Res. 66: 9171-9177.
16. Tagawa, S T, Beltran, H, Vallabhajosula, S, Goldsmith, S J, Osborne, J, Matulich, D, et al. (2010). Anti-prostate-specific membrane antigen-based radioimmunotherapy for prostate cancer. Cancer 116: 1075-1083.
17. Chen, Z, Penet, M-F, Nimmagadda, S, Li, C, Banerjee, S R, Winnard, P T, Jr, et al. (2012). PSMA-targeted theranostic nanoplex for prostate cancer therapy. ACS Nano 6: 7752-7762.
18. Dhar, S, Gu, F X, Langer, R, Farokhzad, O C and Lippard, S J (2008). Targeted delivery of cisplatin to prostate cancer cells by aptamer functionalized Pt(IV) prodrug-PLGA-PEG nanoparticles. PNAS 105: 17356-17361.
19. Dhar, S, Kolishetti, N, Lippard, S J and Farokhzad, O C (2011). Targeted delivery of a cisplatin prodrug for safer and more effective prostate cancer therapy in vivo. PNAS-doi:10,1073/pnas.1011379108.
20. Gu, F, Langer, R and Farokhzad, O C (2009). Formulation/preparation of functionalized nanoparticles for in vivo targeted drug delivery. Methods Mol. Biol. 544: 589-598.
21. Zhao, Y, Duan, S, Zeng, X, Liu, C, Davies, N M, Li, B, et al. (2012). Prodrug strategy for PSMA-targeted delivery of TGX-221 to prostate cancer cells. Mol. Pharm. 9: 1705-1716.
22. Chu, T C, Marks, J W, Lavery, L A, Faulkner, S, Rosenblum, M G, Ellington, A D, et al. (2006). Aptamer: Toxin Conjugates that Specifically Target Prostate Tumor Cells. Cancer Res 66: 5989-5992.
23. Ni, X, Zhang, Y, Ribas, J, Chowdhury, W H, Castanares, M, Zhang, Z, et al. (2011). Prostate-targeted radiosensitization via aptamer-shRNA chimeras in human tumor xenografts. J. Clin. Invest. 121: 2383-2390.
24. Dassie, J P, Liu, X-Y, Thomas, G S, Whitaker, R M, Thiel, K W, Stockdale, K R, et al. (2009). Systemic administration of optimized aptamer-siRNA chimeras promotes regression of PSMA-expressing tumors. Nat. Biotechnol. 27: 839-849.
25. Trouet, A and Jollés, G (1984). Targeting of daunorubicin by association with DNA or proteins: a review. Semin. Oncol. 11: 64-72.
26. Zeman, S M, Phillips, D R and Crothers, D M (1998). Characterization of covalent Adriamycin-DNA adducts. Proc Natl Acad Sci USA 95: 11561-11565.
27. Swift, L P, Cutts, S M, Raphaeli, A, Phillips, D R (2002). Activation of Adriamycin by the pH-dependent Formaldehyde-releasing Prodrug Hexamethylenetetramine. Mol. Cancer Ther. 2: 189-198
28. Wang, A H, Gao, Y G, Liaw, Y C and Li, Y K (1991). Formaldehyde cross-links daunorubicin and DNA efficiently: HPLC and X-ray diffraction studies. Biochemistry 30: 3812-3815.

Titration of Dimeric Aptamer Complex

Titration data (Table 2) confirms that 14 molar equivalents of doxorubicin can be covalently bound to each dimeric aptamer complex (DAC).

TABLE 2

| Dox:DAC ratio | DNA conc μm | Dox Conc μm | calc ratio |
| --- | --- | --- | --- |
| 16x | 0.201 | 2.17 | 10.79602 |
| 24x | 0.17 | 2.41 | 14.17647 |
| 32x | 0.218 | 2.99 | 13.7156 |

The foregoing is illustrative of the present invention, and is not to be construed as limiting thereof. The invention is defined by the following claims, with equivalents of the claims to be included therein.

That which is claimed is:

1. A pharmaceutical composition comprising an aptamer in a pharmaceutically acceptable carrier, wherein:
   said aptamer selectively binds a cancer cell extracellular receptor protein, and
   said aptamer is directly linked by covalent bonding to from 2 to 10 toxin compounds, wherein said covalent bonding comprises a geminal diamine linkage.

2. The composition of claim 1, wherein at least one of said toxin compounds is an anthracycline or a taxane having a free amine.

3. The composition of claim 2, wherein said aptamer is directly linked by covalent bonding to said anthracycline or said taxane at a CpG binding site on said aptamer.

4. The composition of claim 1, wherein the half life of said covalent bonding to the toxin compounds is at least 5 hours in human blood plasma.

5. The composition of claim 1, wherein said aptamer comprises at least one FdUMP.

6. The composition of claim 1, wherein said aptamer is provided as a dimeric complex.

7. The composition of claim 6, wherein said cancer cell extracellular receptor protein is a dimeric protein and said dimeric complex comprises a first nucleic acid that selectively binds to said cancer cell extracellular receptor protein, a second nucleic acid that also selectively binds to said cancer cell extracellular receptor protein, and a linker connecting said first and second nucleic acids.

8. The composition of claim 7, wherein said dimeric protein is prostate specific membrane antigen (PSMA), transferrin receptor, carbonic anhydrase XII, or an ErbB receptor.

9. The composition of claim 7, wherein said linker is double-stranded poly-DNA.

10. The composition of claim 9, wherein said double-stranded poly-DNA comprises at least one CpG binding site.

11. The composition of claim 9, wherein said double-stranded poly-DNA comprises a poly-T/poly-A region, wherein at least one of the T residues is replaced by FdU, or wherein said double-stranded poly-DNA comprises a poly-FdU/poly-A region.

* * * * *

```
                                SEQUENCE LISTING

<160> NUMBER OF SEQ ID NOS: 8

<210> SEQ ID NO 1
<211> LENGTH: 89
<212> TYPE: DNA
<213> ORGANISM: Artificial
<220> FEATURE:
<223> OTHER INFORMATION: Random library sequence
<220> FEATURE:
<221> NAME/KEY: misc_feature
<222> LOCATION: (22)..(68)
<223> OTHER INFORMATION: n is a, c, g, or t

<400> SEQUENCE: 1
gcgaaaacgc aaaagcgaaa annnnnnnnn nnnnnnnnnn nnnnnnnnn nnnnnnnnn       60 nnnnnnnnac agcaatcgta tgcttagca                                      89

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
gcgttttcgc ttttgcgttt t                                              21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
agcattgcta tcgtaagcag a                                              21

<210> SEQ ID NO 4
<211> LENGTH: 48
<212> TYPE: DNA
<213> ORGANISM: Artificial
<220> FEATURE:
<223> OTHER INFORMATION: Dox binding sequence

<400> SEQUENCE: 4
gcgttttcgc ttttgcgttt tgggtcatct gcttacgata gcaatgct                 48

<210> SEQ ID NO 5
<211> LENGTH: 24
<212> TYPE: DNA
<213> ORGANISM: Artificial
<220> FEATURE:
<223> OTHER INFORMATION: DAC sequence

<400> SEQUENCE: 5
cggcaaaaaa aaaaaaaaaa gccg                                           24

<210> SEQ ID NO 6
<211> LENGTH: 24
<212> TYPE: DNA
<213> ORGANISM: Artificial
<220> FEATURE:
<223> OTHER INFORMATION: DAC sequence
```

```
<400> SEQUENCE: 6 cggcttttt tttttttttt gccg                                         24

<210> SEQ ID NO 7
<211> LENGTH: 72
<212> TYPE: DNA
<213> ORGANISM: Artificial
<220> FEATURE:
<223> OTHER INFORMATION: Dimeric aptamer sequence

<400> SEQUENCE: 7
gcgttttcgc ttttgcgttt tgggtcatct gcttacgata gcaatgctcg gcaaaaaaaa    60
aaaaaaaagc cg                                                       72

<210> SEQ ID NO 8
<211> LENGTH: 72
<212> TYPE: DNA
<213> ORGANISM: Artificial
<220> FEATURE:
<223> OTHER INFORMATION: Dimeric aptamer sequence

<400> SEQUENCE: 8
gcgttttcgc ttttgcgttt tgggtcatct gcttacgata gcaatgctcg gcttttttt    60 tttttttgc cg                                                        72
```